United States Patent
Cude et al.

(10) Patent No.: US 8,372,057 B2
(45) Date of Patent: Feb. 12, 2013

(54) LUER LOCK ADAPTER

(75) Inventors: J. Michael Cude, College Grove, TN (US); Raymond Jozwik, Hendersonville, TN (US)

(73) Assignee: Coeur, Inc., Lebanon, TN (US)

( * ) Notice: Subject to any disclaimer, the term of this patent is extended or adjusted under 35 U.S.C. 154(b) by 402 days.

(21) Appl. No.: 12/249,199

(22) Filed: Oct. 10, 2008

(65) Prior Publication Data

US 2010/0094260 A1   Apr. 15, 2010

(51) Int. Cl.
*A61M 25/16* (2006.01)
*A61M 5/31* (2006.01)

(52) U.S. Cl. ........ 604/533; 604/534; 604/535; 604/240; 604/241

(58) Field of Classification Search .................. 604/248, 604/283, 533, 535, 905, 240, 241, 534; 285/334.4, 285/31, 148.19, 148.21, 148.22; 128/214 R, 128/247

See application file for complete search history.

(56) References Cited

U.S. PATENT DOCUMENTS

| | | | | |
|---|---|---|---|---|
| 4,294,250 A | * | 10/1981 | Dennehey | 604/403 |
| 5,312,377 A | * | 5/1994 | Dalton | 604/534 |
| 5,591,143 A | | 1/1997 | Trombley et al. | |
| 6,802,836 B2 | * | 10/2004 | Bouphavichith et al. | 604/534 |
| 2004/0155457 A1 | | 8/2004 | Mejlhede et al. | |
| 2004/0243065 A1 | | 12/2004 | McConnell et al. | |

FOREIGN PATENT DOCUMENTS

| | | |
|---|---|---|
| DE | 3242238 A1 | 5/1984 |
| DE | 20017013 U1 | 12/2000 |
| EP | 0827760 A2 | 3/1998 |
| GB | 632317 | 11/1949 |
| WO | 2007100396 A2 | 9/2007 |

* cited by examiner

*Primary Examiner* — Kevin C Sirmons
*Assistant Examiner* — Bradley Thomas, Jr.
(74) *Attorney, Agent, or Firm* — Hahn Loeser & Parks, LLP

(57) ABSTRACT

An adapter for a medical receptacle having a skirt with an outside diameter and a threaded inside diameter, and a tapered post within the skirt, the adapter includes a proximal end portion having a threaded surface including at least one thread configured to threadingly engage the threaded inside diameter of the skirt, a distal end portion having a surface portion and a cylindrical recess, a conduit positioned between the tapered recess and the cylindrical recess such that the conduit is in fluid communication with both the tapered recess and the cylindrical recess; and a longitudinal axis. The proximal end portion includes a tapered recess defined by a wall, a chamfer, and a seat and the surface portion includes a means for gripping, which in one embodiment may be at least two wings.

20 Claims, 5 Drawing Sheets

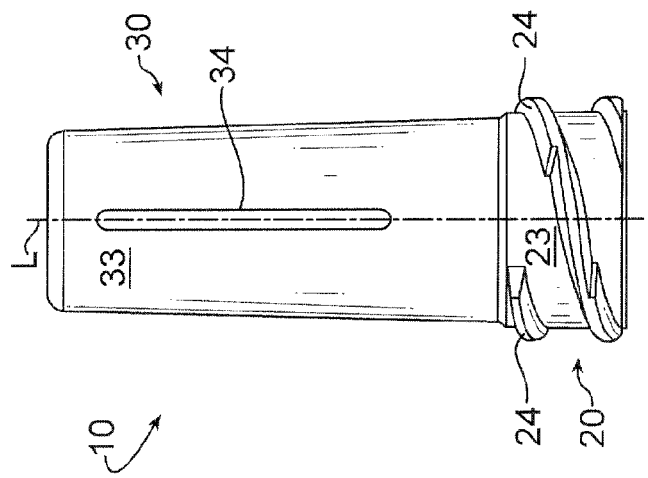
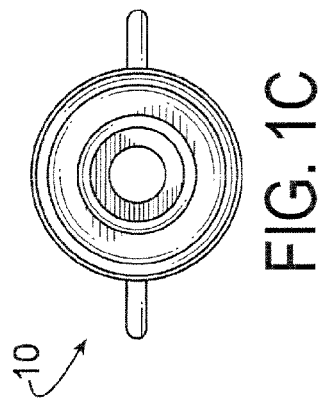
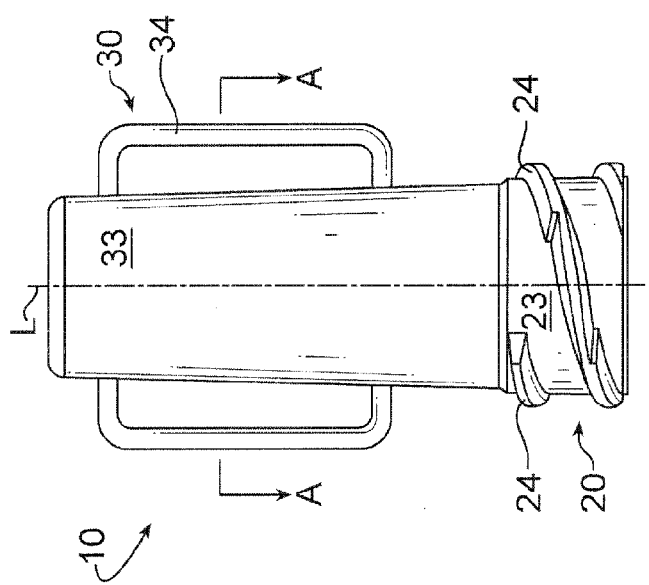

LUER LOCK ADAPTER

TECHNICAL FIELD

The invention pertains to medical equipment, and more particularly to an adapter for medical receptacles, and to a method of attaching an adapter to a medical receptacle.

BACKGROUND OF THE INVENTION

One well known receptacle used to connect and establish fluid communication between different medical components is known as a luer lock. Luer receptacles are widely used to connect syringes to medical instruments, such as needles, and to connect medical conduits to one another. In addition, luer lock receptacles have a standard configuration that allows different sizes and types of instruments to be connected to the same receptacle.

A conventional luer connection assembly typically includes a male luer tip component or fitting having a frustoconical shape which is inserted into a female luer component or fitting having a frustoconical shaped receiving cavity. Opposing conical surfaces come into contact with each other to form a sealed friction fit.

There are two general types of luer connection assemblies. One type is generally referred to as the luer slip, where the connection is maintained by the friction fit between the male luer tip and female luer component. The other type is generally referred to as a luer lock connection, whereby the male luer tip is encircled by an annular locking skirt having a threaded internal surface. The female component includes a corresponding single thread formed about the outer surface. Engaging the threaded skirt to the threaded outside surface establishes the connection between the male luer tip and female component while preventing accidental disconnects.

This conventional luer lock receptacle is used effectively throughout the world, but still has several disadvantages. One disadvantage is that the receptacle is prone to crack and break, particularly at the intersection of the skirt with the syringe barrel and at the intersection of the tapered post with the syringe barrel. This cracking and breaking compromises the strength of the mechanical connection between the receptacle and the adapter, and compromises the fluid tight seals between the receptacle and the adapter. Fluids leaking from the syringe are a particular problem as they can adversely affect a medical procedure, and also present a biological hazard to patients and medical personnel.

This situation may be compounded by medical devices or other instruments connected to a syringe receptacle, which may be relatively long or require aggressive manipulation by medical personnel. For example, harvesting of tissue and cells from different organs of the body, may require a relatively long cannula and aggressive manipulation by physicians, which may damage the receptacle. As there is only one point of contact between the thread on the female adapter and the threaded internal surface of the skirt, aggressive manipulation may cause the thread on the female component to crack or to completely shear off of the component, compromising the integrity of the luer connection.

In addition, the twisting motion required to lock the adapter to the receptacle, can cause the skirt to expand outwardly during engagement of the male threads on the adapter with the female threads on the receptacle. This expansion can also cause cracking and breaking to occur, or can cause micro cracks that lead to cracking and breaking.

In some instances, one receptacle may be used during more than one medical procedure. As each procedure requires the old adapter to be removed from the receptacle and a new adapter to be affixed thereto, there are multiple opportunities for an adapter to be over-torqued. Over-torqueing may result when the individual connecting the adapter to the syringe receptacle continues to twist the adapter after the opposing conical surfaces come into contact with each other to form a sealed friction fit. This over-torqueing may cause the tip of the tapered post to deform at the location where the tip interfaces with the adapter. Such deformation may cause the tip of the tapered post to become occluded, thereby reducing the amount of fluid that may flow through luer connection, thereby rendering the syringe receptacle effectively useless. In extreme instances, over-torqueing may cause the tapered post to fracture at the interface with the syringe receptacle. Over-torqueing may also result in damage at the intersection of the skirt with the syringe barrel and at the intersection of the tapered post with the syringe barrel.

Additionally, luer connections may be used to connect medical devices which are exposed to high pressure, such as injection of contrast media during angiographic procedures. During such procedures, the connection may exposed to pressures that may reach approximately 1200 pounds per square inch. As the rate of fluid injection is monitored and controlled during such angiographic procedures, any occlusion which decreases the amount of fluid being injected will adversely impact the administration of the procedure and result in inaccurate or wholly unusable test results.

Thus, there is a need in the art for an adapter for use in a luer lock connection which may permit users to securely tighten the adapter to the receptacle while preventing the user from over-torqueing the adapter. There is also a need in the art for an adapter which may reduce damage to the adapter and the receptacle from forces exerted perpendicular to the longitudinal axis of the adapter.

SUMMARY OF THE INVENTION

In one embodiment of the subject invention, an adapter for a medical receptacle having a skirt with an outside diameter and a threaded inside diameter, and a tapered post within the skirt, includes a proximal end portion having a threaded surface including at least one thread configured to threadingly engage the threaded inside diameter of the skirt; a distal end portion having a surface portion and a cylindrical recess; a conduit positioned between the tapered recess and the cylindrical recess such that the conduit is in fluid communication with both the tapered recess and the cylindrical recess; and a longitudinal axis. The proximal end portion includes a tapered recess defined by a wall, a chamfer, and a seat and the surface portion includes a means for gripping.

In one aspect of the embodiments of the subject invention, the seat is perpendicular to the longitudinal axis.

In another aspect of the embodiments of the subject invention, the angle formed between the seat and the wall is approximately 90°.

In a further aspect of the embodiments of the subject invention, the angle formed between the seat and the wall is less than 90°.

In a still further aspect of the embodiments of the subject invention, the angle formed between the seat and the chamfer is greater than approximately 90° and less than approximately 180°.

In yet another aspect of the embodiments of the subject invention, the at least one thread is a plurality of threads.

In still yet another aspect of the embodiments of the subject invention, the plurality of threads is two threads.

In even another aspect of the embodiments of the subject invention, the means for gripping is at least two wings extending from the surface portion.

In another aspect of the embodiments of the subject invention, the at least two wings are substantially parallel to the longitudinal axis.

In still another aspect of the embodiments of the subject invention, the at least two wings are angled axially at least 5° from the longitudinal axis.

In yet another aspect of the embodiments of the subject invention, the means for gripping is a plurality of ribs.

In a further aspect of the embodiments of the subject invention, the means for gripping is a plurality of knurls.

In even another aspect of the embodiments of the subject invention, the surface portion further includes a collar projecting therefrom.

In another embodiment of the subject invention, a method for securing an adapter to a medical receptacle having a skirt with an outside diameter and a threaded inside diameter, and a tapered post within the skirt includes the steps of (a) providing an adapter including a proximal end portion having a threaded surface including at least one thread configured to threadingly engage the threaded inside diameter of the skirt, a distal end portion having a surface portion and a cylindrical recess a conduit positioned between the tapered recess and the cylindrical recess such that the conduit is in fluid communication with both the tapered recess and the cylindrical recess; and a longitudinal axis, where the proximal end portion includes a tapered recess defined by a wall, a chamfer, and a seat and the surface portion includes a means for gripping; (b) inserting the tapered post into the tapered recess; and (c) twisting the adapter to engage the at least one thread of the adapter with the threaded inside diameter of the skirt.

In still another embodiment of the subject invention, a method for securing an adapter to a medical receptacle having a skirt with an outside diameter, a threaded inside diameter, and an upper surface, and a tapered post within the skirt includes the steps of (a) providing an adapter comprising a proximal end portion having a threaded surface including at least one thread configured to threadingly engage the threaded inside diameter of the skirt, the proximal end portion including a tapered recess defined by a wall, a chamfer, and a seat, a distal end portion having a surface portion and a cylindrical recess, a conduit positioned between the tapered recess and the cylindrical recess such that the conduit is in fluid communication with both the tapered recess and the cylindrical recess, and a longitudinal axis, wherein the surface portion includes a means for gripping and the proximal end further includes a collar projecting from the threaded surface; (b) inserting the tapered post into the tapered recess; and (c) twisting the adapter to engage the at least one thread of the adapter with the threaded inside diameter of the skirt until the collar contacts the upper surface of the skirt.

BRIEF DESCRIPTION OF THE DRAWINGS

FIG. 1A is side view of a luer lock adapter;

FIG. 1B is a side view of the luer lock adapter of FIG. 1A rotated 90°;

FIG. 1C is a top view of the luer lock adapter of FIG. 1A;

DETAILED DESCRIPTION OF THE INVENTION

Figure 2:
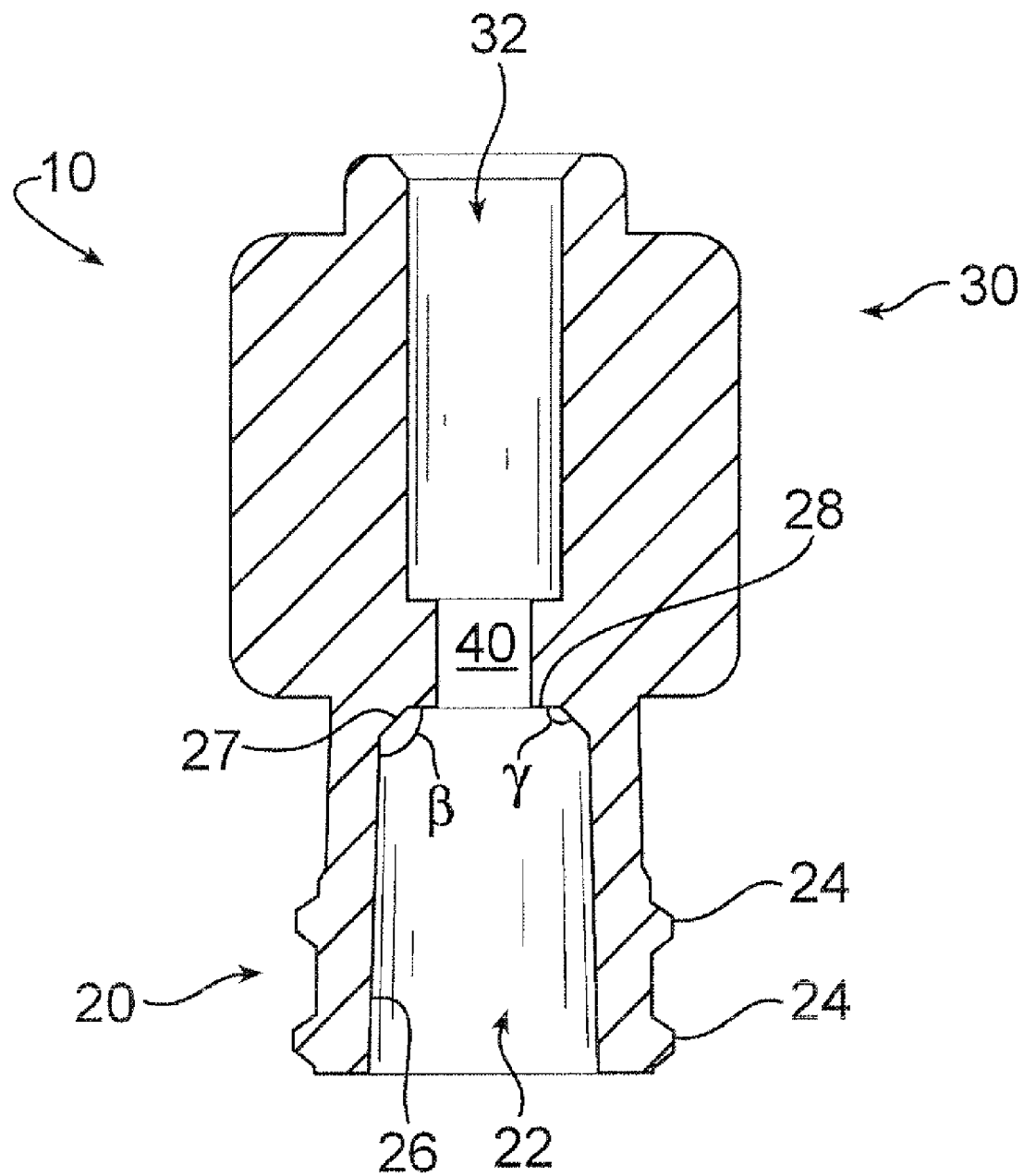
FIG. 2 is a cross-sectional view of the luer lock adapter of FIG. 1A.

Referring now to FIGS. 1A, 1B, 1C and 2, an adapter 10 for attachment to a medical device is illustrated. The adapter 10 may include a proximal end 20 having a tapered recess 22 formed therein. The adapter 10 may also include a distal end 30 having a cylindrical recess 32 formed therein. The adapter 10 may also include a conduit 40 formed between the tapered recess 22 and the cylindrical recess 32. The conduit 40 may be in fluid communication with both the tapered recess 22 and the cylindrical recess 32.

In construction, the adapter 10 may comprise a rigid or semi-rigid material such as metal, hard plastic or a composite. The adapter 10 may be molded, machined or otherwise formed with the required features and dimensions.

Figure 3C:
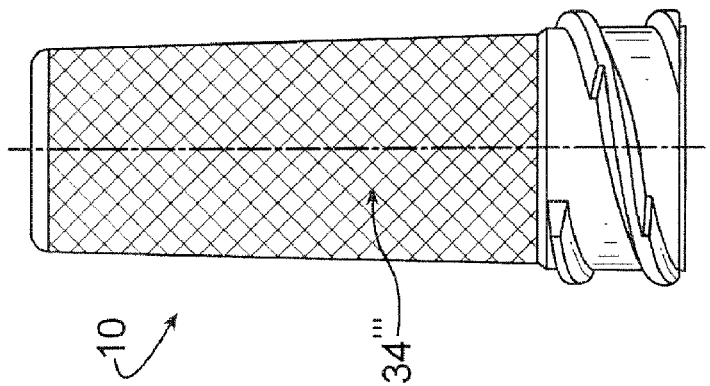
FIG. 3C is a side view of another alternate embodiment of a luer lock adapter.
Figure 3B:
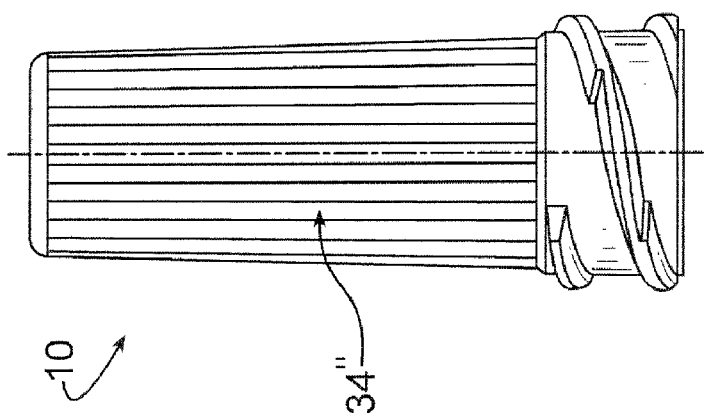
FIG. 3B is a side view of another alternate embodiment of a luer lock adapter.
Figure 3A:
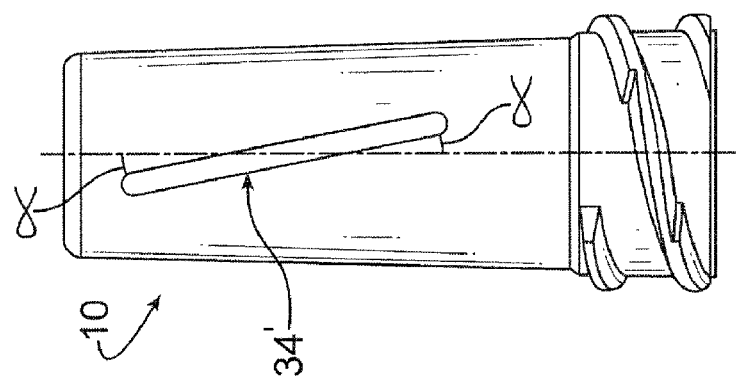
FIG. 3A is a side view of another embodiment of a luer lock adapter.

As shown in FIGS. 1A and 1B, the adapter 10 may be generally cylindrical in shape and may have a longitudinal axis L. The adapter may also include a surface portion 33 which includes a means for gripping 34. In one embodiment, the means for gripping 34 may comprise at least two wings which extend outwardly from the surface portion 33. It is envisioned that the means for gripping 34 are dimensioned such that they may not permit an individual twisting the adapter 10 to achieve sufficient mechanical advantage to over-torque the adapter 10, thereby damaging the adapter and/or the medical device to which the adapter 10 may be attached. The receptacle may be susceptible to damage, for example, at the intersection of the skirt with the syringe barrel as well as at the intersection of the tapered post with the syringe barrel. In an alternate embodiment as shown in FIG. 3A, the means for gripping 34' may include at least two wings which may be spaced approximately 180° apart about the surface portion 33 and are angled axially by an angle α. The angle α may be chosen such that when a user attempts to over-torque the adapter 10, the user's fingers may slip off of the means for gripping, thereby preventing over-torqueing. For example, angle α may be 5°. In other alternate embodiments, the means for gripping may be ribs 34", as shown in FIG. 3B, or knurls 34''', as shown in FIG. 3C.

As shown in FIG. 2, the adapter 10 may include a tapered recess 22 defined by an interior wall 26, a chamfer 27, and a seat 28. In one embodiment, the seat 28 may be perpendicular to the longitudinal axis L. It is also envisioned that the angle between the seat 28 and the wall 26, angle β, may be approximately 90°. Furthermore, it is envisioned that the angle β may be less than 90° in instances where the seat 28 is angled toward and into the tapered recess 22, rather than being oriented approximately perpendicular to the longitudinal axis L. It is also envisioned that the angle between the seat 28 and the chamfer 27, angle γ, may be between approximately 90° and approximately 180°.

Figure 4:
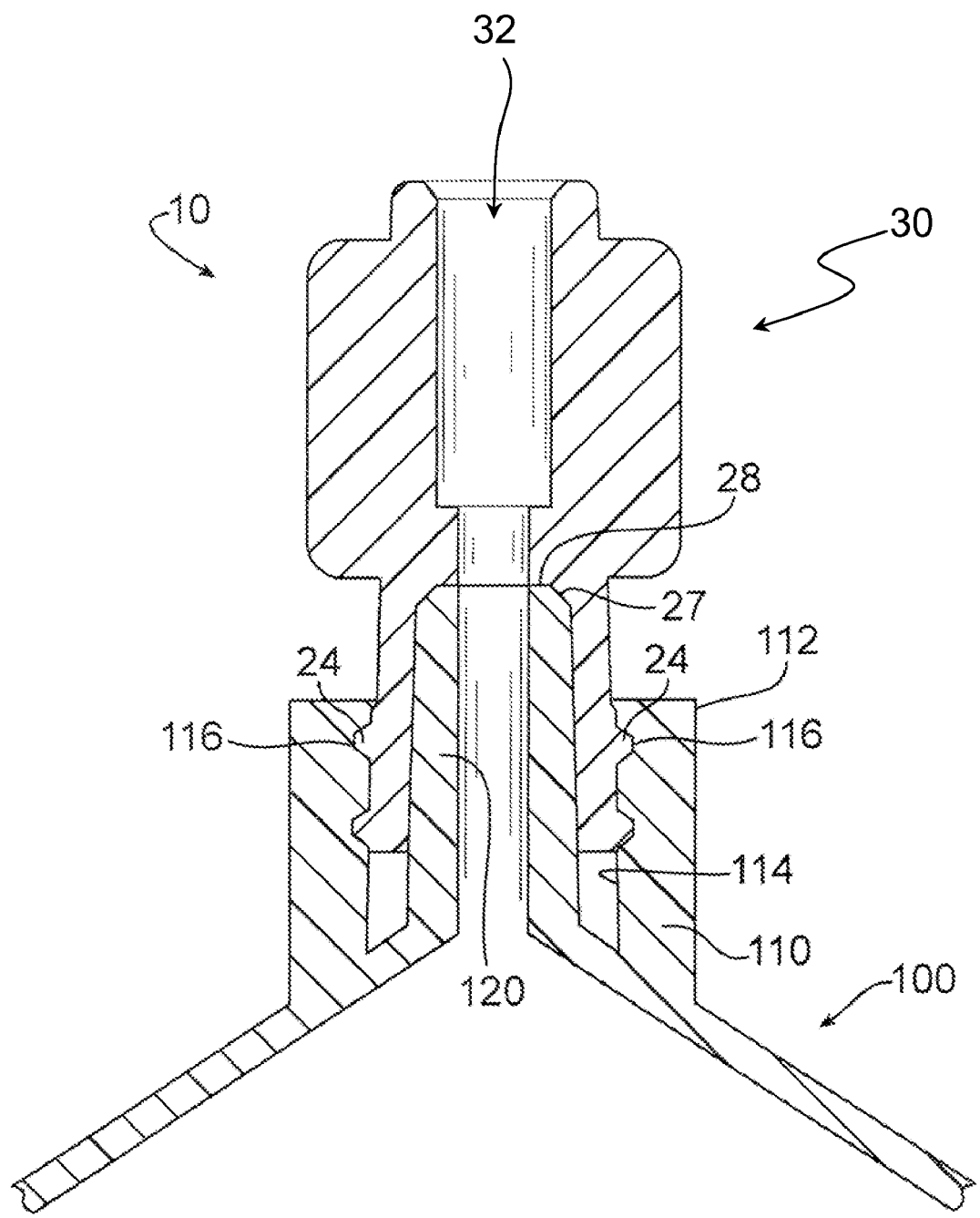
FIG. 4 is a cross-sectional view of the luer lock adapter of FIG. 1A attached to a medical receptacle.

Referring now to FIG. 4, the distal end of the adapter 30 may also include a cylindrical recess 32, into which a medical instrument, including medical tubing or needles, may be affixed by a suitable method such as such as welding, brazing or press fitting. Alternately, the adapter 10 and the medical instrument may be machined or molded from a same piece of material.

Referring again to FIG. 1A, The adapter 10 may also include a proximal end 20 having a threaded surface 23. The threaded surface 23 may include at least one thread 24 extending therefrom. The at least one thread 24 may facilitate threading engagement with a medical receptacle which may have a skirt with an outside diameter and a threaded inside diameter. In one embodiment, the at least one thread 24 may be a plurality of threads. In another embodiment, the at least one thread 24 may be two threads. Specifically, the thread configuration may be of the double-start, double-thread variety.

With reference again to FIG. 4, the adapter 10 may be threadingly attached to medical receptacle 100 having a skirt 110 with an outside diameter 112 and an inside diameter 114 which may include threads 116. The at least one thread 24 may be configured such that the at least one thread 24 may threadingly engage the threads 116 of the inside diameter of the skirt 110. Providing the at least one thread 24 as two threads may result in increased contact between the at least one thread 24 and the threads 116 of the medical receptacle 116. As indicated by the configuration of the at least one thread 24 in FIG. 4, the at least one thread 24 contacts the skirt threads 116 at two points spaced approximately 180° apart on the diameter of the adapter 10. Thus, if a force perpendicular to the longitudinal axis is applied to the adapter 10 from one direction, the at least one thread 24 on the side of the adapter 10 from which the force is applied may tend to deflect upward and contact the top surface of the corresponding thread 116. In contrast, the at least one thread 24 on the opposite side of the adapter 10 from which the force is applied may tend to deflect downward and contact the bottom surface of the corresponding thread 116, thereby creating two points of contact between the adapter 10 and the receptacle 100 and providing additional resistance to the applied force. In contrast, prior art adapters may include only one thread and thus have only one point of contact with the receptacle. As there is no second point of contact between the receptacle and the adapters of the prior art, the force applied to a prior art adapter may likely crack the threads attached to the adapter or in extreme cases, shear the threads from the adapter completely. Thus, it is envisioned that the at least one thread 24 is designed to achieve sufficient mechanical advantage such that this type of damage to the adapter 10, as well damage at the intersection of the skirt 110 with the syringe barrel and at the intersection of the tapered post 120 with the syringe barrel, is thereby reduced when the adapter 10 is subjected to forces perpendicular to its longitudinal axis.

With continued reference to FIG. 4, the adapter 10 may be attached to the receptacle 100 by aligning the tapered post 120 of the receptacle 110 with the tapered recess 22 and pressing the adapter 10 onto the tapered post 120 while simultaneously engaging the at least one thread 24 with the threads 116 of the skirt 110. While twisting the adapter 10, the end of the tapered post 120 may contact the seat 28, at which point the user may feel resistance, which may indicate that the adapter 10 has been fully engaged with the receptacle 100. By contrast, prior art tapered recesses have not included seats such as those presently disclosed, whereby over-torqueing and resultant damage to tapered posts are therefore common occurrences.

Figure 5:
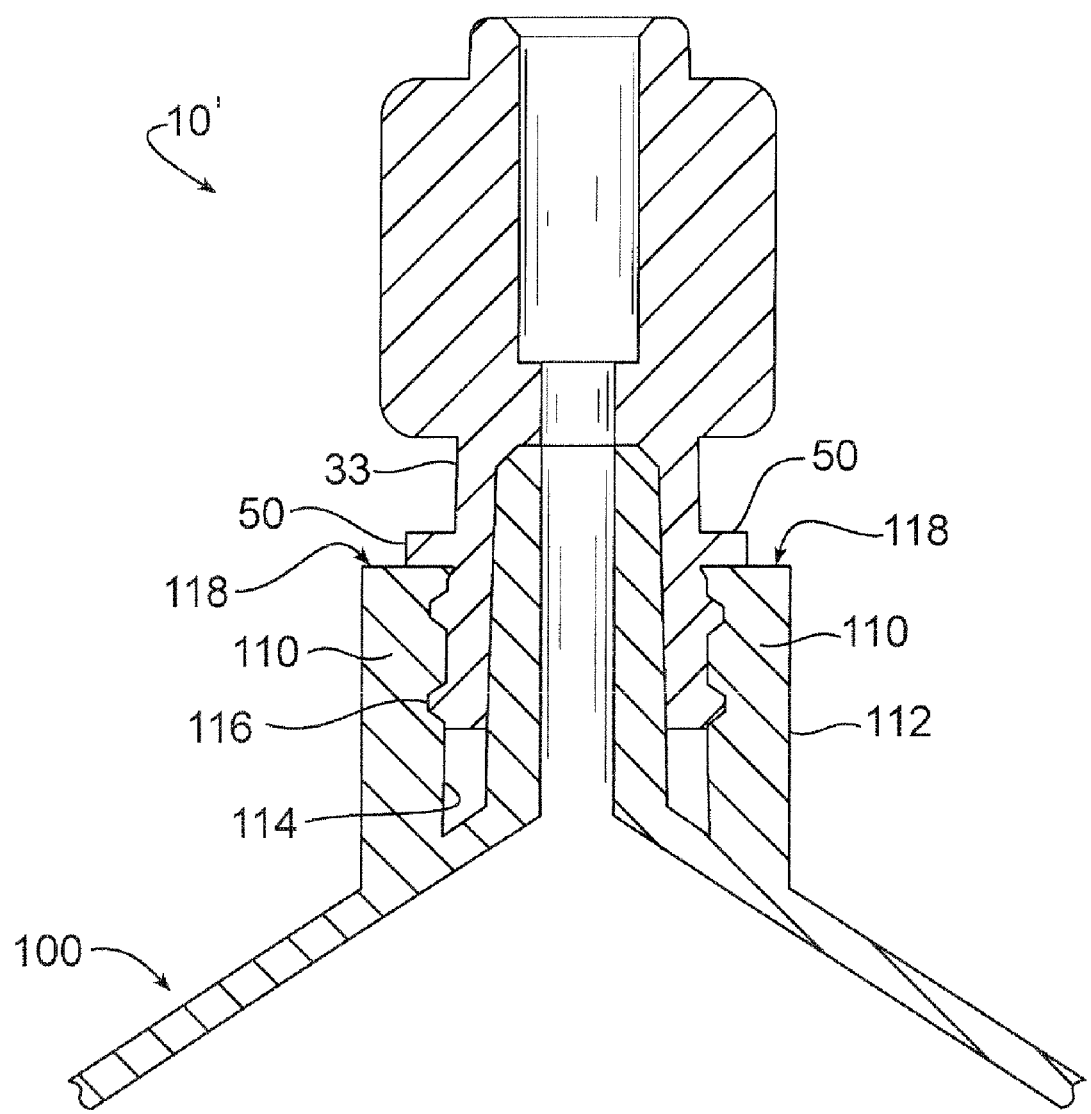
FIG. 5 is a cross-sectional view of an alternate embodiment of a luer lock adapter attached to a medical receptacle.

In an alternate embodiment shown in FIG. 5, the adapter 10' may include a collar 50 which extends from the surface portion 33. Thus, as the adapter 10' is attached to the receptacle 100, the collar 50 may contact a top surface 118 of the skirt 100, such that the collar 50 acts as a mechanical stop which may prevent a user from over-torqueing the adapter 10', thus preventing damage to the adapter 10' and the medical receptacle 100. Furthermore, the collar 50 may also act as a visual cue to the user attaching the adapter 10' to the receptacle 100, in that a gap between the collar 50 and the top surface 118 may be present until the adapter 10' has been sufficiently tightened. Thus, a user may be signaled that the adapter 10' has been sufficiently tightened once any gap has disappeared.

The invention has been described herein with reference to the disclosed embodiments. Obviously, modifications and alterations will occur to others upon a reading and understanding of this specification. It is intended to include all such modifications and alterations insofar as they come within the scope of the appended claims or the equivalence thereof.

What is claimed is:

1. An adapter for a medical receptacle having a skirt with an outside diameter and a threaded inside diameter, and a tapered post within the skirt, the adapter comprising:
   a proximal end portion having a threaded surface including at least one thread configured to threadingly engage the threaded inside diameter of the skirt, the proximal end portion including a tapered recess defined by a wall, a chamfer having a flat transition from the wall to a seat, and the seat having a diameter,
   a distal end portion having a surface portion and a cylindrical recess having a diameter;
   an elongated conduit positioned between the tapered recess and the cylindrical recess such that the conduit is in fluid communication with both the tapered recess and the cylindrical recess and the cylindrical recess and the tapered recess are spaced apart by the length of the conduit, the conduit having a diameter smaller than both the seat diameter and the cylindrical recess diameter; and
   a longitudinal axis;
   wherein the surface portion includes a means for gripping.

2. The adapter of claim 1, wherein the seat is perpendicular to the longitudinal axis.

3. The adapter of claim 1, wherein the angle formed between the seat and the wall is approximately 90°.

4. The adapter of claim 1, wherein the angle formed between the seat and the wall is less than 90°.

5. The adapter of claim 1, wherein the angle formed between the seat and the chamfer is greater than approximately 90° and less than approximately 180°.

6. The adapter of claim 1, wherein the at least one thread is a plurality of threads.

7. The adapter of claim 6, wherein the plurality of threads is two threads.

8. The adapter of claim 1, wherein the means for gripping is at least two wings extending from the surface portion.

9. The adapter of claim 8, wherein the at least two wings are substantially parallel to the longitudinal axis.

10. The adapter of claim 8, wherein the at least two wings are angled axially at least 5° from the longitudinal axis.

11. The adapter of claim 1, wherein the means for gripping is a plurality of ribs.

12. The adapter of claim 1, wherein the means for gripping is a plurality of knurls.

13. The adapter of claim 1, wherein the surface portion further includes a collar projecting therefrom.

14. A method for securing an adapter to a medical receptacle having a skirt with an outside diameter and a threaded inside diameter, and a tapered post within a hub comprising the steps of:
   (a) providing an adapter comprising a proximal end portion having a threaded surface including at least one thread configured to threadingly engage the threaded inside diameter of the skirt, the proximal end portion including a tapered recess defined by a wall, a chamfer having a flat transition from the wall to a seat, and the seat having a diameter, a distal end portion having a surface portion and a cylindrical recess having a diameter;

an elongated conduit positioned between the tapered recess and the cylindrical recess such that the conduit is in fluid communication with both the tapered recess and the cylindrical recess and the cylindrical recess and the tapered recess are spaced apart by the length of the conduit, the conduit having a diameter smaller than both the seat diameter and the cylindrical recess diameter; and a longitudinal axis;

wherein the surface portion includes a means for gripping, (b) inserting the tapered post into the tapered recess; and (c) twisting the adapter to engage the at least one thread of the adapter with the threaded inside diameter of the medical receptacle.

15. The method of claim 14, wherein the seat is perpendicular to the longitudinal axis.

16. The method of claim 14, wherein the means for gripping is at least two wings extending from the surface portion.

17. The method of claim 14, wherein the at least one thread is a plurality of threads.

18. The method of claim 17, wherein the plurality of threads is two threads.

19. The method of claim 14, wherein the surface portion further includes a collar projecting therefrom.

20. A method for securing an adapter to a medical receptacle having a skirt with an outside diameter, a threaded inside diameter and an upper surface, and a tapered post within a hub comprising the steps of:

(a) providing an adapter comprising a proximal end portion having a threaded surface including at least one thread configured to threadingly engage the threaded inside diameter of the skirt, the proximal end portion including a tapered recess defined by a wall, a chamfer having a flat transition from the wall to a seat, and the seat having a diameter, a distal end portion having a surface portion and a cylindrical recess having a diameter, an elongated conduit positioned between the tapered recess and the cylindrical recess such that the conduit is in fluid communication with both the tapered recess and the cylindrical recess and the cylindrical recess and the tapered recess are spaced apart by the length of the conduit, the conduit having a diameter smaller than both the seat diameter and the cylindrical recess diameter, and a longitudinal axis, wherein the surface portion includes a means for gripping and the proximal end further includes a collar projecting from the threaded surface;

(b) inserting the tapered post into the tapered recess; and (c) twisting the adapter to engage the at least one thread of the adapter with the threaded inside diameter of the skirt until the collar contacts the upper surface of the skirt.

* * * * *